US00PP30734P2

(12) United States Plant Patent
Bourne

(10) Patent No.: US PP30,734 P2
(45) Date of Patent: Jul. 23, 2019

(54) GRAPEVINE NAMED 'SV33-122-37'

(50) Latin Name: ***Vitis* spp.**
Varietal Denomination: SV33-122-37

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 16/350,141

(22) Filed: Oct. 2, 2018

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ..... A01H 5/08; A01H 6/88
See application file for complete search history.

*Primary Examiner* — Annette H Para
(74) *Attorney, Agent, or Firm* — Baker Manock & Jensen, PC; Eric C. Cole

(57) ABSTRACT

A new and distinct variety of grapevine plant named 'SV33-122-37' particularly characterized by its ellipsoidal to ovate shaped, seedless, red skinned berries which are medium-large, sweet, with a fruity *Vitis labrusca* flavor and which have tender texture. Productivity is high, with spur pruning only needed for a full crop.

2 Drawing Sheets

Latin name of the genus and species of the plant claimed: The plant claimed relates to a new and distinct variety of *Vitis* spp.

Variety denomination: The plant claimed shall be known as 'SV33-122-37'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis* spp. and hereinafter referred to as grapevine named 'SV33-122-37'. As used herein, 'grapevine' refers to all plant parts including, vines, canes, tendrils, leaves, fruit and roots of 'SV33-122-37'. Grapevine named 'SV33-122-37' is the result of an effort to produce a table grape with flavor characteristics similar to cultivars descending from *Vitis labrusca* L. such as 'Concord', 'Campbell's Early', and others. This new cultivar originated from a cross conducted in May 2012 near McFarland, Calif. between the seedless cultivar 'Marquis' (U.S. Plant Pat. No. 11,012) and pollen parent 'SV26-69-250' (unpatented). Clusters of fruit resulting from the hybridization were harvested six weeks after crossing and the resultant ovules were cultured on 'McCown's Woody Plant Medium' at a temperature of 22° C. for twelve weeks. Subsequently, the resultant embryonic plants were cultured in the same medium in the laboratory under twelve hours of light from standard fluorescent lamps at 26.4° C. The seedlings were then planted in a standard greenhouse flat and were grown in the greenhouse at 26.4° C. with 12 hours' illumination under high pressure sodium vapor lamps. The seedling population of 56 plants was planted in the field in the spring of 2013 near Delano, Calif. The new grapevine was selected from this seedling population on Aug. 22, 2014. It was then propagated by cuttings and bench grafted to 'Freedom' (unpatented) rootstock in 2015. The present invention has been found to retain its distinctive characteristics through two successive asexual propagations.

Grapevine named 'SV33-122-37' differs from its female parent 'Marquis' (U.S. Plant Pat. No. 11,012) in that grapevine named 'SV33-122-37' has dark red berries with thin skin while 'Marquis' (U.S. Plant Pat. No. 11,012) has white skinned fruit with a thicker skin.

Grapevine named 'SV33-122-37' differs from its male parent 'SV26-69-250' (unpatented) in that grapevine named 'SV33-122-37' has berries with distinctive fruity flavor typical of *Vitis vinifera* while 'SV26-69-250' (unpatented) has black skinned berries with neutral flavor and larger size than the extant cultivar.

Grapevine named 'SV33-122-37' differs from the commercial cultivar 'IFG Twenty-Three' (U.S. Plant Pat. No. 28,667) in that grapevine named 'SV33-122-37' has berries with more tender texture than 'IFG Twenty-Three' (U.S. Plant Pat. No. 28,667), and grapevine named 'SV33-122-37' ripens in late August while 'IFG Twenty-Three' (U.S. Plant Pat. No. 28,667) ripens in mid-September. Additionally, grapevine named 'SV33-122-37' has berries which are brighter red than 'IFG Twenty-Three' (U.S. Plant Pat. No. 28,667) which are reddish-black.

SUMMARY OF THE INVENTION

The following are the most outstanding and distinguishing characteristics of the ripe fruit of this new variety when grown under normal horticultural practices near McFarland, Calif. Some of the characteristics may vary depending upon changes in crop load and change of location of cultivation.

1. Dark red to reddish black berry color;
2. Slightly soft to medium firm texture; and
3. Medium sized berries with a thin skin and strong, fruity taste.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The first photograph of shoots, leaves and a fruit cluster taken from a four year old plant grown in a field near McFarland, Calif. in 2018. The second photograph was taken in 2018 of a cluster of fruit on a two year old vine, grown in a field near Bakersfield, Calif.

DETAILED BOTANICAL DESCRIPTION

Figure 1:
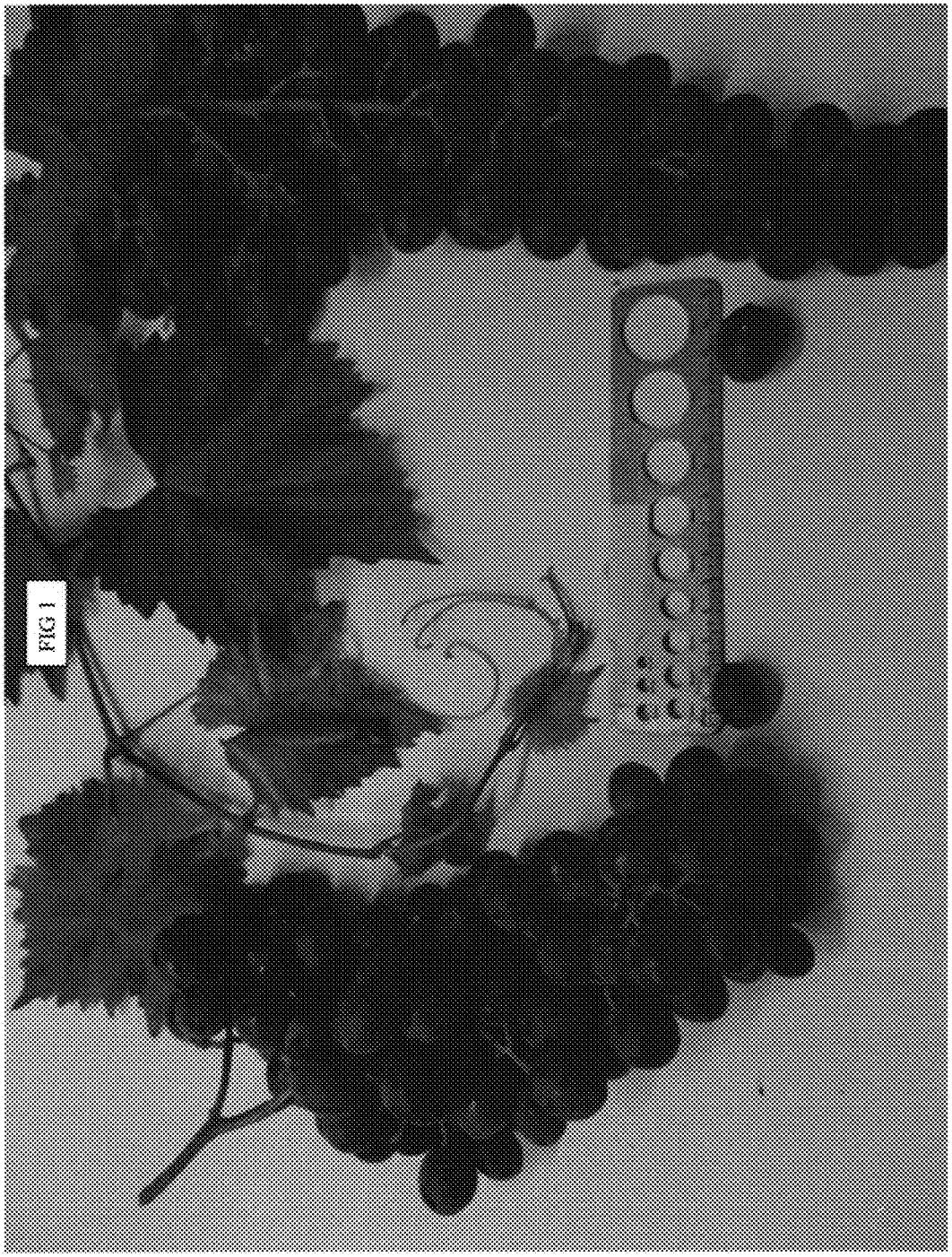
FIG. 1 Fruit cluster with shoots, leaves, tendrils and shoot tip.
Figure 2:
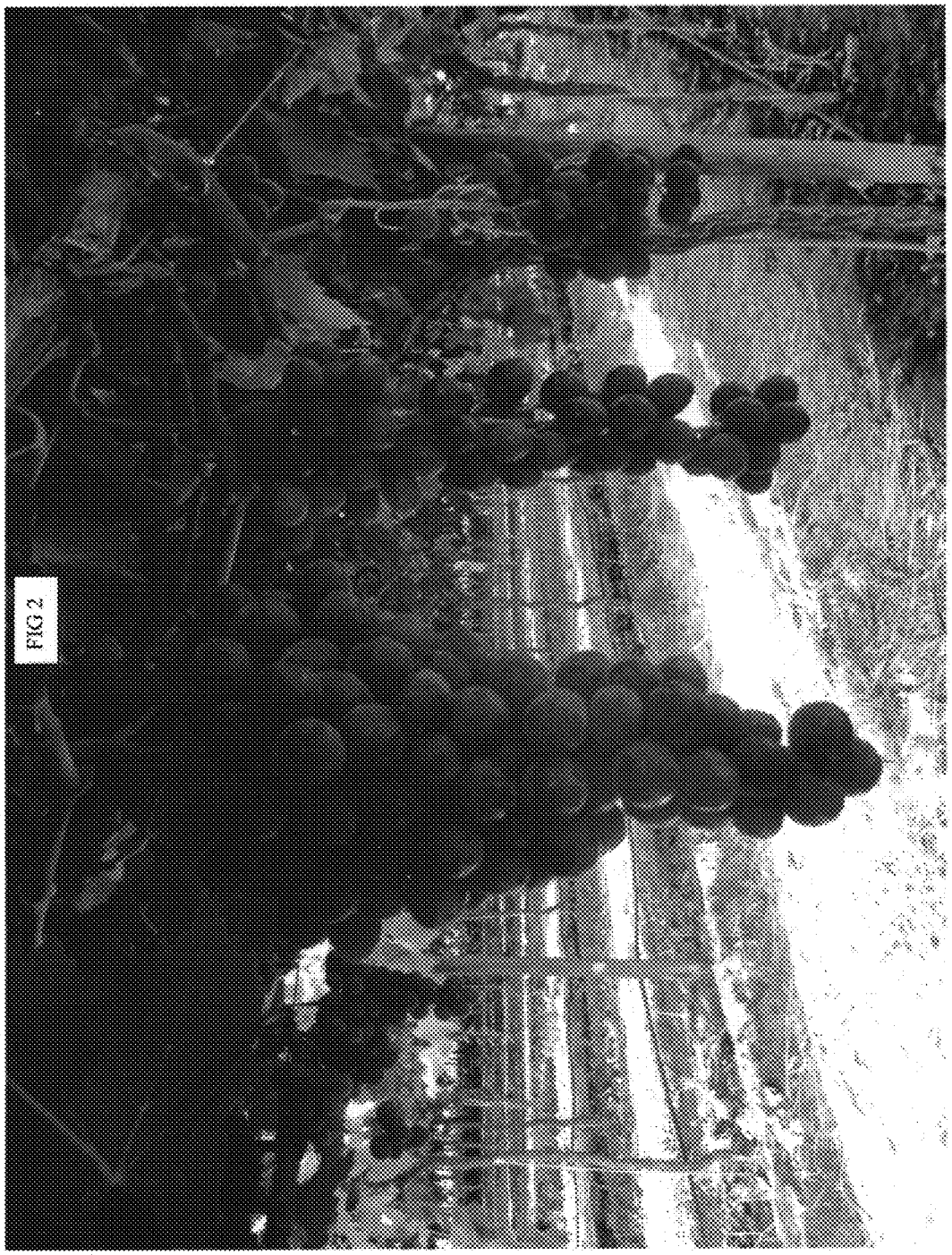
FIG. 2 Fruit clusters on vine.

The following detailed description sets forth the distinctive characteristics of grapevine named 'SV33-122-37'. Descriptions of the new invention apply to vines of grapevine named 'SV33-122-37' grown on 'Freedom' (unpatented) rootstock at a density of 1,537 vines per hectare grown near McFarland, Calif. in 2018. These vines were in their fourth year of full production, having been planted in 2013. These descriptions are believed to apply generally to the new variety grown under similar circumstances elsewhere. References to color correspond to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:
- *Family*.—Vitaceae.
- *Botanical name*.—*Vitis vinifera*.
- *Variety name*.—'SV33-122-37'.

Plant:
- *Vigor*.—High; vines spur-pruned and shoot thinned to 32 shoots.
- *Density of foliage*.—Heavy.
- *Productivity*.—Very productive when pruned to spurs with canes, up to 32,000 kg/hectare.
- *Hardiness*.—Hardiness observed to 0° C.
- *Rootstock*.—'Freedom' (unpatented).

Trunk:
- *Shape*.—Broadly elliptical.
- *Straps*.—Long, split.
- *Surface texture*.—Shaggy.
- *Inner bark color*.—RHS Greyed orange group 174B.
- *Outer bark color*.—RHS Brown group 200B.

Growing tips:
- *Apex*.—Open.
- *Density of prostrate hairs on tip*.—Dense.
- *Density of erect hairs on tip*.—Absent.
- *Color*.—RHS Yellow Green Group 145B.
- *Anthocyanins*.—Present at the tips of the young, expanding leaves.
- *Shape*.—Flattened.
- *Shoot attitude*.—Semi-erect.

Young shoot:
- *Density of erect hairs on node*.—Absent.
- *Density of erect hairs on internode*.—Absent.
- *Density of prostrate hairs on node*.—Sparse.
- *Density of prostrate hairs on internode*.—Sparse.
- *Internode color, lower surface*.—RHS Yellow green group 146C.
- *Internode color, upper surface, in sun*.—RHS Red purple group 61B.

Young leaves:
- *Color of young leaves*.—RHS Yellow Green group 144A.
- *Density of prostrate hairs, lower surface, between veins*.—Sparse.
- *Density of erect hairs lower blade surface, between veins*.—Absent.
- *Density of prostrate hairs on main veins, lower surface*.—Abundant, very short.

Mature leaves:
- *Average blade length*.—15.6 cm.
- *Average blade width*.—18.5 cm.
- *Size of blade*.—Large.
- *Shape*.—Pentagonal.
- *Anthocyanin coloration of main veins on the upper side of the blade*.—Absent.
- *Mature leaf profile*.—Undulating.
- *Blistering* (*upper surface*).—Absent.
- *Leaf blade tip*.—Apex tip within plane of blade.
- *Margins*.—Lobed, serrated, undulating.
- *Apex*.—Narrowly acuminate.
- *Bases*.—Sagittate.
- *Thickness*.—Medium.
- *Undulation of blade between main and lateral veins*.—Slight.
- *Shape of teeth*.—Conical; both sides convex.
- *Length of teeth*.—3-10 mm.
- *Ratio length/width of teeth*.—Variable: about equal to much broader than long.
- *General shape of petiole sinus*.—Wide open; ovate in outline.
- *Tooth at petiole sinus*.—Absent
- *Petiole sinus limited by veins*.—Absent.
- *Shape of upper lateral sinus*.—Closed; some leaves without clearly defined upper lobes.
- *Prostrate hairs between veins* (*lower surface*).—Sparse.
- *Erect hairs between veins* (*lower surface*).—Absent.
- *Prostrate hairs on main veins* (*lower surface*).—Sparse.
- *Density of erect hairs on main veins* (*lower surface*).—Absent.
- *Prostrate hairs on main veins* (*upper surface*).—Sparse.
- *Prostrate hairs between veins* (*upper surface*).—Sparse.
- *Upper surface*.—Summer color: RHS Green group 139A. Surface texture: Smooth. Surface appearance: Dull. Goffering of blade: Absent.
- *Lower surface*.—Summer color: RHS Green group 143A. Anthocyanin coloration of main veins on lower leaf surface: Absent. Anthocyanin coloration on laterals: No. Glossiness: Low. Pubescence: Prostrate hairs between veins and on main veins. Surface texture: Rough. Surface appearance: Dull.

*Petiole*.—Length: 12.6 cm. Length of petiole compared to middle vein: Slightly shorter. Density of prostrate hairs: Sparse. Density of erect hairs: Absent. Shape of base of petiole sinus: Wide open. Color: In shade: RHS Yellow green group 144B. In sun: RHS Yellow green group 144B with streaks of RHS Red purple group 61A.

Tendrils:

*Color*.—In shade: RHS Yellow green group 144A.

*Form*.—Bifurcated or trifurcated.

*Number of successive tendrils*.—At most, 2.

*Density of prostrate hairs*.—Sparse.

Flowers:

*Flower sex*.—Perfect.

*Position of first flowering nodes*.—Second or third.

*Number of inflorescences per shoot*.—Usually two.

*Date of full bloom*.—Early, May 3$^{rd}$.

Fruit:

*Ripening period*.—Mid-season.

*Date of ripening*.—August 25th at McFarland, Calif.

*Use*.—Fresh market.

*Keeping quality*.—Good.

*Shipping quality*.—Good.

*Solids-sugar*.—20 brix at full maturity.

*Bunch*.—Size: Medium. Length (peduncle excluded): 26.8 cm. Width: 11.4 cm. Weight: Natural: 542 g. Density: Well-filled, but loose. Number of berries: 100. Form: Cylindrical with an occasional long shoulder.

*Peduncle*.—Length: 3.5 cm. Lignification: Slight. Color: RHS Yellow green group 144A.

*Berry*.—Size: Medium large. Weight: 5.2 g. Shape: Elliptical to ovate. Presence of seeds: Seedless; most berries develop one or two tiny ovule traces about 5 mm in length. Cross section: Circular. Dimensions: Longitudinal axis: About 2.3 cm. Horizontal axis: About 2.0 cm. Skin color (without bloom): In shade of canopy: RHS Red purple group 59A; clusters exposed to the sun: RHS Purple group N77A. Juiciness of flesh: Very juicy. Berry firmness: Tender. Particular flavor: Neutral. Bloom (cuticular wax): Heavy. Pedicel length: Variable, 7-15 mm. Berry separation from pedicel: Difficult.

*Skin*.—Thickness: Thin. Texture: Tender. Reticulation: Absent. Roughness: Absent. Tenacity: Tenacious to flesh. Tendency to crack: Resistant.

Disease and insect resistance: Moderately susceptible to powdery mildew which may be controlled with standard fungicides in California.

Having thus described and illustrated our new variety of grapevine, I claim:

1. A new and distinct variety of grapevine plant named 'SV33-122-37', substantially as illustrated and described herein.

* * * * *